United States Patent [19]

Fujine et al.

[11] Patent Number: 4,600,566
[45] Date of Patent: Jul. 15, 1986

[54] METHOD OF LITHIUM ISOTOPE SEPARATION

[75] Inventors: Sachio Fujine; Keiichiro Saito; Koreyuki Shiba, all of Ibaraki, Japan

[73] Assignee: Japan Atomic Energy Research Institute, Tokyo, Japan

[21] Appl. No.: 575,981

[22] Filed: Feb. 1, 1984

[30] Foreign Application Priority Data

Feb. 8, 1983 [JP] Japan ................................. 58-19259

[51] Int. Cl.⁴ .............................................. C01D 15/00
[52] U.S. Cl. ...................................... 423/179.5; 423/2; 423/181
[58] Field of Search ..................... 423/157, 2, 7, 181, 423/179.5

[56] References Cited

U.S. PATENT DOCUMENTS

| | | | |
|---|---|---|---|
| 3,701,638 | 10/1972 | Hagiwara | 423/179.5 |
| 3,953,568 | 4/1926 | Seko et al. | 423/7 |
| 4,080,337 | 3/1978 | Cram | 260/296 H |
| 4,224,429 | 9/1980 | Lehn et al. | 526/183 |
| 4,331,785 | 5/1982 | Chamberlin et al. | 423/181 |
| 4,367,072 | 1/1983 | Vögtle et al. | 436/501 |
| 4,373,070 | 2/1983 | Soula | 525/332.2 |

OTHER PUBLICATIONS

Lehn et al., *J. Am. Chem. Soc.*, 97 (#23), pp. 6700–6707, Nov. 12, 1975.
Perret et al., *Proc. 2nd U.N. Intl. Conf. Peaceful Uses of Atomic Energy*, vol. 4, pp. 595, 598–599, (1958).

*Primary Examiner*—Edward A. Miller
*Attorney, Agent, or Firm*—Browdy and Neimark

[57] ABSTRACT

A method of lithium isotope separation by using a cryptand resin as an adsorbent is herein disclosed.

14 Claims, 4 Drawing Figures

APPARATUS USED FOR
LITHIUM ISOTOPE SEPARATION

Fig. 1  APPARATUS USED FOR LITHIUM ISOTOPE SEPARATION
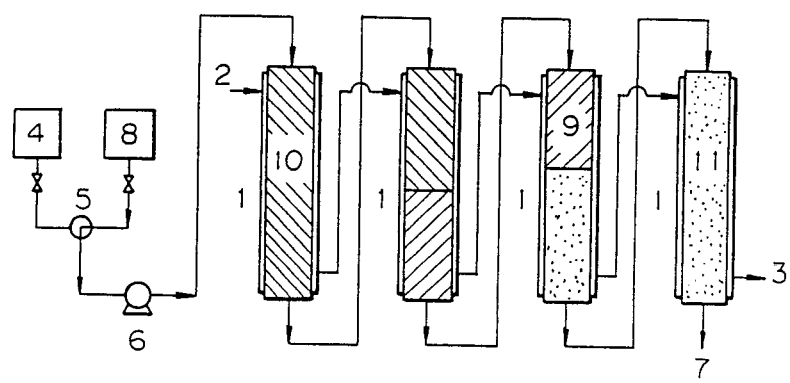
Fig. 2  CHROMATOGRAM OBTAINED IN EXAMPLE 1
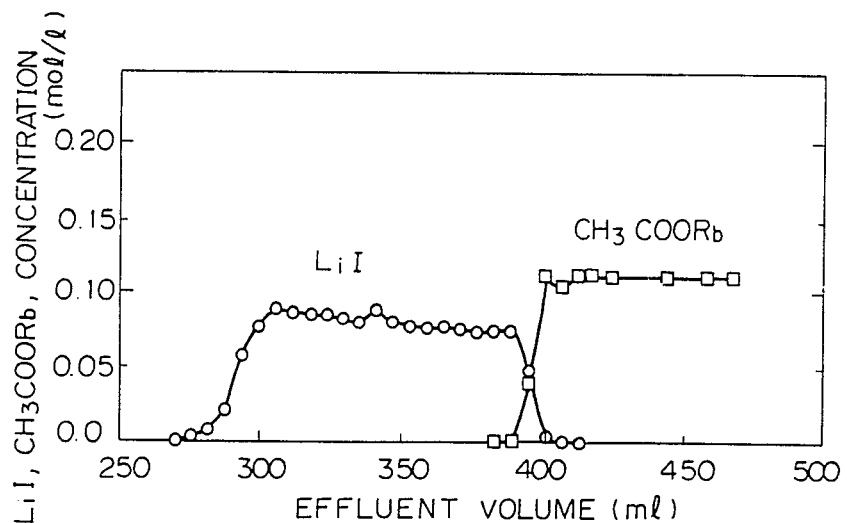

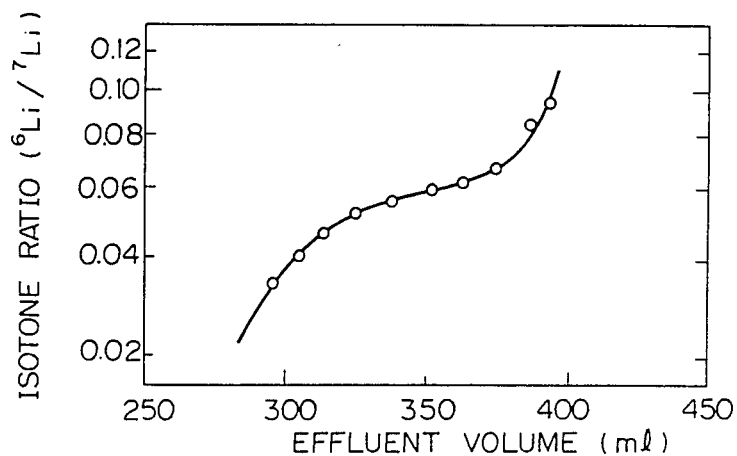
Fig. 3 Li ISOTOPE CONCENTRATION PROFILE OF Li ADSORPTION BAND OBTAINED IN EXAMPLE 1.
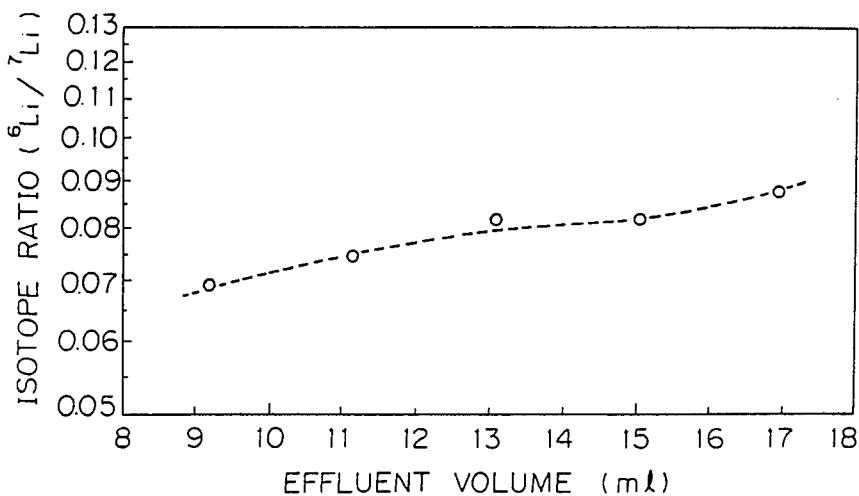
Fig. 4 Li ISOTOPE CONCENTRATION PROFILE OF Li, ADSORPTION BAND OBTAINED IN EXAMPLE 2.

METHOD OF LITHIUM ISOTOPE SEPARATION

BACKGROUND OF THE INVENTION

1. Field of the Invention

The present invention relates to a method of separating lithium isotopes. More specifically, the invention relates to a method of lithium isotope separation by using a cryptand resin as an adsorbent.

2. Description of the Prior Art

Lithium consists of two stable isotopes, lithium-6 ($^6$Li) having a normal abundance of 7.5 at.% and lithium-7 ($^7$Li) with an abundance of 92.5 at.%. Recent years have seen an ever-increasing demand for these two lithium isotopes in nuclear energy applications. Lithium-6, with its high thermal neutron absorption cross section (ca. 947 barns) is used in shields against radioactive rays, control rods or lithium breeding blankets in fusion reactors. Lithium-7 having excellent thermodynamic and heat transfer characteristics and a low thermal neutron absorption cross section is used as an agent to control the acidity of the primary cooling water is pressurized-water reactors.

Conventionally, industrial lithium isotope separation is carried out by the amalgam method or displacement chromatography using a strong acid cation-exchange resin as an adsorbent. However, the amalgam method uses a large quantity of mercury and may cause environmental pollution or endanger the health of the related personnel. Conventional displacement chromatography is not highly effective because the single-stage separation factor is only 1.001 to 1.005. Therefore, it has long been desired to develop a new method for separating lithium isotopes without the defects of the conventional techniques.

SUMMARY OF THE INVENTION

The general object of the present invention is to provide a new method of separating lithium isotopes.

A specific object of the present invention is to provide a lithium isotope separation method using a cryptand resin as a adsorbent.

Other objects and the advantages of the present invention will become apparent by reading the following description in conjunction with the accompanying drawings, wherein:

FIG. 1 is a sketch of one embodiment of the apparatus used to implement the method of the present invention;

FIG. 2 is a chromatogram obtained in Example 1 which will be described later in this specification; and FIGS. 3 and 4 respectively show the Li isotope ratio profiles obtained in Examples 1 and 2.

DETAILED DESCRIPTION OF THE INVENTION

The method of the present invention is characterized by using a cryptand resin as an adsorbent. This term represents a resin having bicyclic azacrown ethers bound chemically to an organic polymer matrix. There is no strict definition of the crown compounds, but generally they include macrocyclic compounds (also referred to as multidentate macrocyclic compounds, multiheteromacrocycles or macroheterocycles) having contained in the ring structure a donor hetero atom such as O, N or S and which are capable of confining cations in the cavity. The structures of two illustrative crown compounds are shown below.

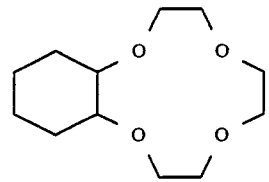

cyclohexyl-12-crown-4

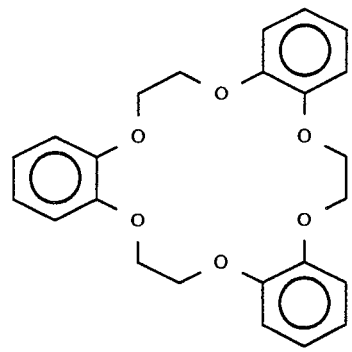

tribenzo-18-crown-6

Crown compounds having oxygen as the only donor atom are called crown ethers. Crown ethers having part of the donor oxygen atoms replaced by N(NH, NR) are called azacrown ethers. Bicyclic azacrown ethers in a three-dimensional cage form having two nitrogen bridgeheads

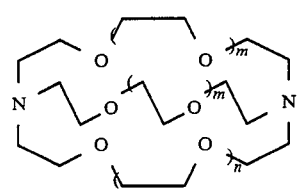

are called cryptands which will be coordinated with metals to form complexes called cryptates. Typical cryptands are listed below, together with their structures and names, according to both simplified and IUPAC nomenclature.

(I)

[structure]

(i) m=n=0; [1,1,1]-cryptand; 4,10,15-trioxa-1,7-diazabicyclo[5,5,5]heptadecane (IUPAC)

(ii) m=0, n=1; [2,1,1]-cryptand; 4,7,13,18-tetraoxa-1,10-diazabicyclo[8,5,5]eicosane (IUPAC)

(iii) m=1, n=0; [2,2,1]-cryptand; 4,7,13,16,21-pentaoxa-1,10-diazabicyclo[8,8,5]tricosane (IUPAC)

(iv) m=n=1; [2,2,2,]-cryptand; 4,7,13,16,21,24-hexaoxa-1,10diazabicyclo[8,8,8]hexacosane (IUPAC)

(v) m=1, n=2; [3,2,2]-cryptand; 4,7,10,16,19,24,27-heptaoxa-1,13-Δdiazabicyclo[11,8,8]nonacosane (IUPAC)

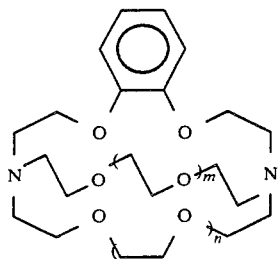

(i) m=n=1; [2B,2,2,]-cryptand; 4,13-(ethanoxyethanoxyethano)-4H,13H-1,7,10,16,4,13-benzotetraoxdiazabicyclootaΔdecine-2,3,5,6,8,9,11,12,14,15-decahydro (IUPAC)

(ii) m=n=0; [2B,1,1]-cryptand;

(iii) m=0, n=1; [2B,2,1]-cryptand.

The cryptands have a cavity of a specific diameter and will entrap in the interior of a spatial lattice a metallic ion that is equal in size to that cavity diameter so as to form a stable complex (or cryptate). Thus, the cryptands have ion selectivity and high complex stability constants. Cryptand resins have such cryptands bound chemically to organic polymer matrices.

The cryptand resins particularly useful in the present invention are illustrated by the following structural formulas (1) and (2). They are respectively composed of [2B,2,2]-cryptand and [2B,2,1]-cryptand bound chemically to an organic polymer matrix such as styrene-divinylbenzene polymer. These cryptand resins are insoluble in water or organic solvents, stable in acids or alkalis and respectively have Na+ exchange capacities of 0.35 meq/g and 0.25 meq/g.

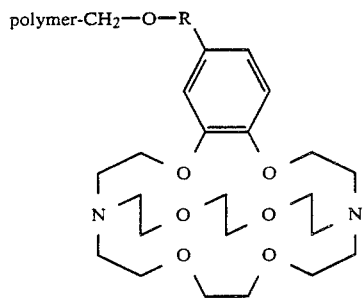

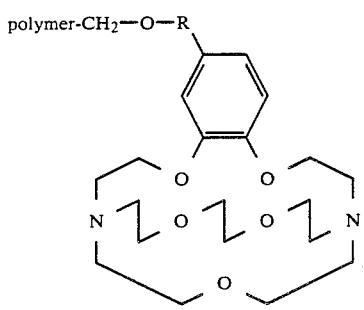

The method of the present invention starts with a regeneration and conditioning step wherein methyl alcohol or ethyl alcohol is passed through a chromatographic column packed with a suitable cryptand resin. Then, a specific amount of solution of lithium salt is fed through the column to form lithium band on the column. Thereafter, a solution containing ions having a higher complex stability constant than the lithium ion is passed through the column so as to effect displacement chromatography wherein the lithium adsorption band is moved without any change in length. By this procedure, $^6Li$ having a higher affinity for the adsorbent (cryptand resin) is concentrated at the trailing end of the lithium band on the column and $^7Li$ which adsorbs less strongly to the resin is concentrated at the leading end.

Suitable lithium salts are in the form of iodides, bromides, acetates, hydroxides, chlorides, sulfides and nitrates. Iodide and bromide ions having a relatively small electronegativity are preferred because they provide an ion exchange capacity about twice as much as that of other anions and achieve a lithium isotope separation factor of 1.03–1.06. The lithium salts used in the present invention must have high solubility in solvents. Preferred solvents are methyl alcohol and ethyl alcohol that will not adsorb strongly to the cryptand resin.

The process of the present invention may also be carried out in the presence of a holding ion by the following procedure. First, a solution containing ion species having a lower complex stability constant K (the stability of the complex with cryptand) than the lithium ion is passed through the column so as to adsorb that ion species on the cryptand resin. Then, a given amount of a lithium salt solution is fed through the column, followed by the passage of a solution containing ion species having a higher complex stability constant than the lithium ion. As in the first embodiment, this procedure ensures displacement chromatography wherein the lithium adsorption band can be moved through the column without any change in the band length. Lithium-6 which adsorbs strongly to the resin is concentrated at the trailing end of the lithium band and $^7Li$ which adsorbs less strongly is concentrated at the leading end.

The constants of the stability of the complexes (cryptates) formed between the cryptand resins and metallic ions are given in Journal of the American Chemical Society, 97 231, Nov. 12, 1975. Examples of the ion species having smaller complex stability constants than the lithium ion are $Cs^+$ and $Mg^{2+}$, and those having higher stability constants are $Na^+$, $K^+$, $Rb^+$, $Ca^{2+}$, $Sr^{2+}$ and $Ba^{2+}$.

The column in which $^6Li$ has been separated from $^7Li$ by the method of the present invention can be regenerated by simply passing water or an aqueous acetic acid solution through the column. In this way, a lithium adsorption band of a maximum length can be moved through a minimum number of columns in order to obtain two separate lithium isotopes in high concentrations.

One embodiment of the method of the present invention which uses no holding ion is hereunder described by reference to FIG. 1 showing an example of the apparatus used to implement that method. The apparatus includes four liquid chromatographic columns 1 each consisting of an inner cylinder packed with a suitable cryptand resin and an outer shell equipped with a jacket through which warm water is passed to hold the inner cylinder at a constant temperature that assures high adsorption efficiency. This water is fed in at an inlet 2, passes through the jacket of each column and is discharged at an outlet 3, from which it is returned to the inlet 2. Methyl alcohol or ethyl alcohol in a tank 4 flowing through a valve 5 is forced with a plunger pump 6 to pass successively through the columns and is discharged at an effluent outlet 7. After this conditioning of the adsorbent (cryptand resin), the valve 5 is switched and a lithium salt solution in a tank 8 is pumped through the columns to form a given length of lithium adsorption band 9. Thereafter, a displacing solution having ion species with a higher complex stability constant than that of the lithium ion is fed to the tank 8, from which it is passed through the columns in order to move the adsorption band toward the column at the final stage. In FIG. 1, the lithium adsorption band 9 is formed both in the lower part of the second column and in the upper part of the third column. The adsorption band of the displacing ion species indicated at 10 is formed in the entirety of the first column and in the upper part of the second column. The solvent used to condition the columns comes ahead of the lithium adsorption band and is indicated at 11. By following this procedure, $^6$Li which adsorbs strongly to the resin is obtained as a concentrate at the trailing end whereas $^7$Li that adsorbs less strongly is concentrated at the leading end.

The present invention is described in greater detail by reference to the following examples which are given here for illustrative purposes only. In the examples, a cryptand resin having a lithium exchange capacity of ca. 0.12 meq/ml was used as an adsorbent. It was composed of [2B,2,1]-cryptand particles (250–500 μm) chemically bound to a styrenedivinylbenzene resin. The lithium isotope ratio ($^6$Li/$^7$Li) was determined by optical spectrometry using a hollow cathode lamp as a light source calibrated by mass spectrometry. The lithium, sodium and rubidium concentrations were determined by flame photometry.

EXAMPLE 1

A series of four chromatographic columns was packed with the cryptand resin. Each column having an inside diameter of 8 mm and being 1 m long was equipped with a jacket through which warm water (40° C.) was caused to flow to maintain the column at a constant temperature. The resin in each column was thoroughly conditioned with methanol. A methanol solution of lithium iodide (80 ml) was poured through the respective columns overhead, and subsequently, a methanol solution of rubidium acetate was kept supplied into the columns at a superficial velocity of 0.99 m/hr. The resulting lithium adsorption band of a substantially constant length moved through the columns over a distance of 4 m, and an effluent was obtained from the bottom of the fourth column. The concentration profiles of lithium iodide and rubidium acetate in the effluent are shown in FIG. 2. The isotope ratio profile of the effluent lithium adsorption band is shown in FIG. 3, from which one can see that the first effluent had a $^6$Li/$^7$Li ratio of 3.5% and the last run had a value of 11%.

EXAMPLE 2

Two series-connected jacketed chromatographic columns having an inside diameter of 3 mm and 1 m long were packed with the cryptand resin and thoroughly conditioned with methanol. Water (40° C.) was poured through the jacket of each column to maintain it at a constant temperature. A methanol solution of cesium chloride (0.12 mol/1,000 ml) was poured through both columns. Then, each column was supplied with 4.5 ml of a methanol solution of lithium acetate (0.12 mol/1,000 ml) to form a lithium adsorption band. Subsequently, a methanol solution of sodium acetate (0.12 mol/1,000 ml) was continuously supplied through the respective columns at a superficial velocity of 1.78 m/hr. The lithium adsorption band moved through the columns over a distance of 2 m without any substantial change in the band length, and an effluent was obtained from the bottom of the second column. The isotope ratio profile of the effluent is shown in FIG. 4.

What is claimed is:

1. A method of separating lithium-6 from lithium-7 in a displacement chromatography process which comprises passing a lithium salt methanol solution into a cryptand resin packed column so as to adsorb a predetermined amount of lithium ions on the resin thereby creating a lithium adsorbed band of given length, and subsequently passing through the column a solution of ion species having a higher complex stability constant than the lithium ion to displace the lithium adsorbed band without substantially changing its length, thereby obtaining a rate of separation of 1.03–1.06, the resin containing cryptand groups having the following structural formula (I) or (II)

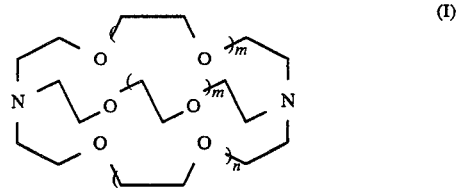

(I)

(i) m=n=0; [1,1,1]-cryptand; 4,10,15-trioxa-1,7-diazabicyclo[5,5,5]heptadecane(IUPAC)
(ii) m=0, n=1; [2,1,1]-cryptand; 4,7,13,18-tetraoxa-1,10-diazabicyclo[8,5,5]eicosane(IUPAC)
(iii) m=1, n=0; [2,2,1]-cryptand; 4,7,13,16,21-pentoaxa-1,10-diazabicyclo[8,8,5]tricosane(IUPAC)
(iv) m=n=1; [2,2,2]-cryptand; 4,7,13,16,21,24-hexaoxa-1,10diazabicyclo[8,8,8]hexacosane(IUPAC)
(v) m=1, n=2; [3,2,2]-cryptand; 4,7,10,16,19,24,27-heptaoxa-1,13-Δdiazabicyclo[11,8,8]nonacosane(IUPAC)

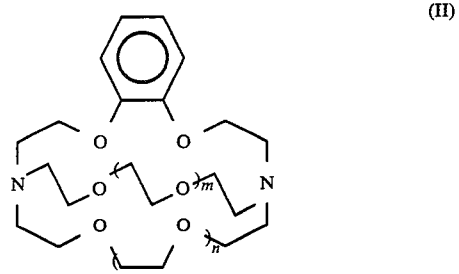

(II)

(i) m=n=1; [2B,2,2]-cryptand; 4,13-(ethanoxyethanoxyethano)-4H,13H-1,7,10,16,4,13-benzotetraoxadiazabicyclootaΔdecine-2,3,5,6,8,9,11,12,14,15-decahydro(IUPAC)
(ii) m=n=0; [2B,1,1]-cryptand;
(iii) m=0, n=1; [2B,2,1]-cryptand.

2. A method according to claim 1 wherein the lithium salt is selected from the group consisting of lithium iodide, lithium bromide, lithium acetate, lithium hyroxide, lithium chloride, lithium sulfide, and lithium nitrate.

3. A method according to claim 1 wherein the cryptand resin comprises [2B,2,2]-cryptand bound chemically to an organic polymer matrix.

4. A method according to claim 1 wherein the cryptand resin comprises [2B,2,1]-cryptand bound chemically to an organic polymer matrix.

5. A method according to claim 1 wherein the ion species having a higher complex stability constant than the lithium ion is selected from among $Na^+$, $K^+$, $Rb^+$, $Ca^{2+}$, $Sr^{2+}$ and $Ba^{2+}$.

6. A method of separating lithium-6 from lithium-7 in a displacement chromatography process which comprises passing into a cyptand resin packed column a solution of ion species having a lower complex stability constant than lithium ion so as to adsorb said ion species on the resin, subsequently passing through the column a lithium said alcohol solution so as to adsorb lithium ions on the resin thereby creating a lithium adsorbed band of given length, and finally feeding through the column a solution of ion species having a higher complex stability constant than substantially chaning its length, and obtaining a rate of separation of 1.03–1.06, the resin containing cryptand groups having the following structural formula (I) or (II)

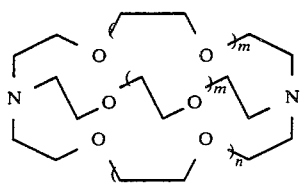

(i) m=n=0; [1,1,1]-cryptand; 4,10,15-trioxa-1,7-diazabicyclo[5,5,5]heptadecane(IUPAC)

(ii) m=0, n=1; [2,1,1]-cryptand; 4,7,13,18-tetraoxa-1,10-diazabicyclo[8,5,5]eicosane(IUPAC)

(iii) m=1, n=0; [2,2,1]-cryptand; 4,7,13,16,21-pentaoxa-1,10-diazabicyclo[8,8,5]tricosane(IUPAC)

(iv) m=n=1; [2,2,2]-cryptand; 4,7,13,16,21,24-hexaoxa-1,10diazabicyclo[8,8,8]hexacosane(IUPAC)

(v) m=1, n=2; [3,2,2,]-cryptand; 4,7,10,16,19,24,27-heptaoxa-1,13-Δdiazabicyclo[11,8,8]nonacosane(IUPAC)

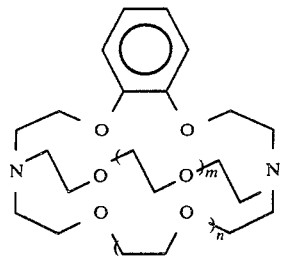

(i) m=n=1; [2B,2,2]-cryptand; 4,13-(ethanoxyethanoxyethano)-4H,13H-1,7,10,16,4,13-benzotetraoxadiazabicyclootaΔdecine-2,3,5,6,8,9,11,12,14,15-decahydro(IUPAC)

(ii) m=n=0; [2B,1,1]-cryptand;

(iii) m=0, n=1; [2B,2,1]-cryptand.

7. A method according to claim 6 wherein the ion species having a lower complex stability constant than the lithium ion is $Cs^+$ or $Mg^{2+}$.

8. A method according to claim 6 wherein the lithium salt is selected from the group consisting of lithium iodide, lithium bromide, lithium acetate, lithium hydroxide, lithium chloride, lithium sulfide, and lithium nitrate.

9. A method according to claim 6 wherein the cryptand resin comprises [2B,2,2]-cryptand bound chemically to an organic polymer matrix.

10. A method according to claim 6 wherein the cryptand resin comprises [2B,2,1]-cryptand bound chemically to an organic polymer matrix.

11. A method according to claim 6 wherein the ion species having a higher complex stability constant than the lithium ion is selected from among $Na^+$, $K^+$, $Rb^+$, $Ca^{2+}$, $Sr^{2+}$ and $Ba^{2+}$.

12. A method of separating lithium-6 from lithium-7 in a displacement chromatography process, comprising passing a lithium salt solution in a solvent of methanol or ethanol into a [2B,2,1] cryptand resin packed column so as to adsorb a predetermined amount of lithium ions on the resin thereby creating a lithium adsorbed band of a given length, and displacing said lithium adsorbed band without substantially changing its length and obtaining a high rate of 1.03–1.06 separation by passing through the column a solution of an ion species having a higher complex stability to constant than the lithium ion.

13. A method according to claim 12 wherein said solvent is methanol.

14. A method according to claim 13 wherein said ions species having a higher complex stability constant than the lithium ion is rubidium acetate.

* * * * *